United States Patent [19]

Nakano et al.

[11] Patent Number: 4,747,952
[45] Date of Patent: May 31, 1988

[54] METHOD AND APPARATUS FOR PLASMA TREATMENT

[75] Inventors: Akiyoshi Nakano; Yoshimichi Harada, both of Okayama; Yasuzo Kirita, Toyonaka; Tadashi Miyahara, Kurashiki; Yoshio Yagiri, Kurashiki; Michiko Ueda, Kurashiki; Yasunori Ueda, Kurashiki, all of Japan

[73] Assignee: Kuraray Co., Ltd., Japan

[21] Appl. No.: 902,127

[22] Filed: Sep. 2, 1986

Related U.S. Application Data

[63] Continuation of Ser. No. 704,765, Feb. 21, 1985, abandoned.

[30] Foreign Application Priority Data

Feb. 24, 1984 [JP] Japan ................................. 59-34813
Jun. 1, 1984 [JP] Japan ............................... 59-113495

[51] Int. Cl.⁴ ..................... B01D 13/00; B01D 17/038
[52] U.S. Cl. .................................... 210/650; 210/104;
210/110; 210/257.2; 210/259; 210/295;
210/321.65; 210/434; 210/744; 210/782;
210/805
[58] Field of Search ................... 210/86, 90, 104, 110,
210/111, 116, 134, 137, 257.2, 259, 295, 321.1,
335, 433.2, 927, 434, 321.6, 321.65, 634, 649,
650, 651, 744, 782, 805

[56] References Cited

U.S. PATENT DOCUMENTS

| | | | |
|---|---|---|---|
| 3,814,249 | 6/1974 | Eaton | 210/86 |
| 3,830,234 | 8/1974 | Kopp | 210/90 X |
| 4,013,564 | 3/1977 | Nose | 210/434 |
| 4,243,532 | 1/1981 | Tsuda et al. | 210/321.1 X |
| 4,350,156 | 9/1982 | Malchesky | 210/434 X |
| 4,350,594 | 9/1982 | Kawai et al. | 210/295 X |
| 4,397,747 | 8/1983 | Ikeda | 210/321.1 X |

FOREIGN PATENT DOCUMENTS 57-64058 4/1982 Japan.
59-8967 1/1984 Japan.

OTHER PUBLICATIONS

Malchesky, P. S. et al, "On-Line Separation...", Art. Organs, vol. 4, No. 3, pp. 205-207, Aug. 1980.

Primary Examiner—Richard V. Fisher
Assistant Examiner—W. Gary Jones
Attorney, Agent, or Firm—Kramer, Brufsky & Cifelli

[57] ABSTRACT

Separation apparatus capable of separating plasma into high molecular weight substances and low molecular weight substances containing albumin, regardless of whether plasma is obtained by separation of corpuscular components in a continuous centrifugal separator or in a batch-type centrifugal separator. The apparatus comprises a filtration membrane module, a plasma feeding circuit connecting the centrifugal separator with the filtration membrane module, a plasma return circuit for returning to a patient purified plasma freed of high molecular weight substances, a supplemental fluid circuit for supplying additional fluid to the plasma return circuit, and a condensed plasma discharge circuit for disposal of high molecular weight substances. The apparatus is controlled independently of the centrifugal separator.

6 Claims, 5 Drawing Sheets

METHOD AND APPARATUS FOR PLASMA TREATMENT

This application is a continuation of application Ser. No. 704,765 filed Feb. 21, 1985, now abandoned.

BACKGROUND OF THE INVENTION

1. Field of the Invention

This invention relates to an apparatus for plasma treatment capable of operating as a part of systematized unit when a filtration membrane module thereof is properly connected to any of centrifugal separators of two kinds different from each other in performance mechanism. By means of such a systematized unit as above, pathogenic substances and harmful substances as immunocompounds, immunoglobulin association, and nucleic acid contained in blood can efficiently be removed.

2. Description of Prior Art

It has become apparent recently that an abnormal increase in the quantity of high-molecular-weight substance is greatly causative of the origination and conditions of various diseases such as: autoimmune diseases including rheumatism, SLE, myasthenia gravis, Goodpasture syndrome, and idiopathic thrombocytopenic purpura; abnormal metabolism including multiple myeloma and macrogobulinemis; and hyperviscosity syndrome; whereby plasmapheresis has come into wide use for the purpose of removing high-molecular-weight substances. Plasmapheresis is a process to separate blood into plasma and a corpuscular fraction first, remove harmful high-molecular-weight substances from separated plasma component, and then return treated plasma component thus treated together with previously separated corpuscular fraction to the patient's body.

Among conventional methods of separating blood into plasma and a corpuscular fraction, there has been a membrane separation method using a filtration membrane module and a centrifugal separation method using a centrifugal separator. Known methods of plasma separation using the membrane module include the following:

(1) A method wherein, after separating blood into plasma and a corpuscular fraction through plasma separation membrane, a plasma fraction containing harmful substances is removed and a fresh plasma fraction in quantity corresponding to that of the removed plasma fraction is mixed with corpuscular component and returned to the patient's body.

(2) A method wherein, after separating blood into plasma and a corpuscular fraction through plasma separation membrane, a plasma fraction containing harmful substances is brought into contact with adsorbent so as to be adsorbed and removed thereby, and the plasma fraction thus treated is again mixed with corpuscular component and returned to the patient's body. (U.S. Pat. No. 4,013,564; U.S. Pat. No. 4,243,532)

(3) A method wherein, after separating blood into plasma and a corpuscular fraction through plasma separation membrane, plasma component is further separated into low-molecular-weight substances containing albumin and high-molecular-weight substances through plasma treatment membrane, and then purified plasma component free of high-molecular substances containing harmful substances is mixed with corpuscular component and returned to the patient's body. (U.S. Pat. No. 4,350,594; U.S. Pat. No. 4,397,747)

(4) A method wherein, after separating blood into plasma and a corpuscular fraction through plasma separation membrane, plasma fraction is cooled so that high-molecular-weight substances containing harmful substances are caused to gel, the produced gel is removed by filtration membrane, and only such low-molecular-weight substances as pass through the filtration membrane are returned to the patient's body after being mixed with corpuscular fraction. (Artificial Organs, Vol 4, No. 3, pp. 205–207, June, 1980.

On the other hand, the following methods are known as plasmapheresis depending on the centrifugal separation methods:

(1) A method wherein, after separating blood into plasma and a corpuscular fraction by means of centrifugal separator, plasma fraction containing harmful substances is removed and fresh plasma in quantity corresponding to that of corpuscular component is mixed with corpuscular component and returned to the patient's body.

(2) A method wherein, after separating blood into plasma and a corpuscular fraction by means of a centrifugal separator, plasma fraction is separated into high-molecular-weight substances and low-molecular-weight substances by the filtration membrane module and purified plasma from which high-molecular-weight substances alone are removed is returned to the patient's body together with corpuscular component. (Japan Laid-open Patent, Nos. 64,058/82 and 8,967/84.

Among said plasmapheresis methods, plasma exchange therapy is followed by a problem in securing healthy persons' plasma to be transfused into patients' bodies and also secondary effects such as infection caused by other kinds of pathogenic organisms or contraction of serum sickness occurring with transfusion of healthy person's plasma into the patient's body, and therefore transfusion of the patient's own purified plasma is regarded as preferable. Above all, a method of separating blood into plasma and a corpuscular fraction by means of a centrifugal separator and treating plasma fraction by the filtration membrane module is quite safe and excellent in that a fall in separation efficiency as a problem in separation of blood by the filtration membrane module and risky hemolysis are never caused. However, blood treatment by means of a system of combination of the centrifugal separator with the filtration membrane module is scarcely performed these days. The reason for the above fact is considered as follows:

Centrifugal separators in use today for plasma separation are of two kinds different from each other in performance mechanism, that is:

(1) An apparatus of continuous operation type in which blood is continuously fed into the centrifugal bowl at one side and corpuscular fraction and plasma are individually and continuously taken out from the bowl at the other side. (IBM 2,997: Travenol CS-3,000)

(2) An apparatus of batch type in which blood is fed into the bowl at one side and plasma fraction alone is continuously taken out from the bowl at the other side whereas corpuscular fraction is collected in the bowl until when blood letting is stopped immediately after corpuscular fraction sensing means senses corpuscular fraction overflowing the bowl and flowing into the plasma outlet tube, and then corpuscular fraction collected in the bowl are taken out from the blood feeding port. (Haemonetics V-50, Haemonetics PEX) In the case of connecting the centrifugal separator that has been used hitherto with a filtration membrane module, the control circuit of the centrifugal separator must be modified for using closed circuits each exclusive for the centrifugal separator or the module and adapting the control system of the centrifugal separator to control a pump to be connected to the filtration membrane module. Further, the use of exclusive closed circuits prevents the module from being connected to a centrifugal separator whose performance mechanism is different from that of the separator now in use.

SUMMARY OF THE INVENTION

Accordingly, an object of this invention is to provide a plasma treatment apparatus whose filtration membrane module for treating plasma can appropriately be connected to any of centrifugal separators of two kinds different from each other in performance mechanism so as to form a systematized unit.

Another object of this invention is to provide a plasma treatment apparatus to be controlled independently of the control system in the centrifugal separator and capable of operating as a systematized unit when connected to the centrifugal separator.

This invention provides an apparatus for plasma treatment which is connected to a centrifugal separator disposed in the extracorporeal circuit so as to separate plasma component separated from blood by the centrifugal separator into high-molecular-weight substances and low-molecular-weight substances containing albumin by means of filtration membrane module and to return purified plasma freed of high-molecular-weight substances to the body of the patient, and is characterized by providing: a plasma feeding circuit for connecting the centrifugal separator disposed in said extracorporeal circuit with the filtration membrane module; a plasma reservoir bag in said circuit; means for sensing the fluid level in said bag; a plasma feeding pump in which the fluid flow rate can be adjusted while controlled in association with said fluid level sensing means so as to fix the fluid level within a predetermined range; a circuit for returning purified plasma containing albumin and freed of high-molecular-weight substances by said filtration membrane module to the patient's body; a purified plasma reservoir vessel in said circuit; a purified plasma delivery pump in which the fluid flow ratio between plasma introduced into the filtration membrane and purified plasma delivered therefrom is set at a predetermined value while controlled in association with said plasma feeding pump; and further a condensed plasma discharge pump in which the quantity of discharged high-molecular-weight substances is set at a predetermined value in the condensed plasma discharge circuit containing from the filtration membrane module.

BRIEF DESCRIPTION OF THE DRAWINGS

FIGS. 4 and 6 represent an example of an apparatus of this invention used as a part of the system depending on a single-arm method by which corpuscular fraction and purified plasma are mixed together and then returned to the human body; and, FIG. 7 is a perspective view of a monitoring unit for an apparatus for plasma treatment according to this invention.

DETAILED DESCRIPTION OF THE INVENTION

This invention relates to a plasma treatment apparatus which is connected to the centrifugal separator so as to provide a system for separating plasma fraction separated from blood by the centrifugal separator into high-molecular-weight substances and low-molecular-weight substances containing albumin by means of a filtration membrane module and returning purified plasma component freed of high-molecular-weight substances to the patient's body. As a centrifugal separator to be connected to the plasma treatment apparatus of this invention, any of the abovesaid continuous operation type one and batch type one can be used.

As a filtration membrane module for plasma separation in the plasma treatment apparatus, applicable is a module incorporating flat membranes or hollow fiber membranes. Particularly, a module incorporating hollow fiber membranes is desirable in view of easy fabrication and readiness to miniaturization. Filtration membranes used for the abovesaid module selectively separate plasma component into high-molecular-weight substances and low-molecular-weight substances and permit optional setting of a fractionated molecular weight according to the purpose. For example, in the case of autoimmune disease as major one of those to which a therapy using the apparatus of this invention is applied, fractionated molecular weight can be set at a value of 100,000. Pathogenic substances causative of autoimmune diseases are often present in the form bound to γ-globulin whose molecular weight is about 160,000 and, therefore, it is desirable to remove such substances as having molecular weight greater than 160,000 and to return albumin having molecular weight of 67,000 lower than 160,000 and being useful for living body to the patient's body. Therefore, when setting a fractioned molecular weight at 100,000 and γ-globulin can sharply be fractionated from albumin. A value of fractionated molecular weight for said filtration membrane should be set according to molecular weight of pathogenic sustances to be treated and, in addition to the example referred to above, a fractionated molecular weight is set at a value between 100,000 and 200,000 when immunocompound is a cause of the disease. Any kind of filtration membrane may be used as far as capable of fractionating or separating plasma component under pressure and, in this sense, such membranes as having ultrafiltration capability can widely be used. Accordingly, no particular limit is placed on the structure of membrane and uniform microporous membrane and asymmetrical membrane are all usable.

Materials for filtration membranes of such properties as above are polyvinyl alcohol (PVA) type polymers, ethylene-vinyl alcohol (EVA) copolymers, cellulose derivatives (e.g., cellulose acetate), polyolefins, polyacrylonitrites, polyamides, polyesters, polysulfones and the like.

Among those described above, PVA type, EVA type, cellulose derivatives, and polysulfones which are excellent in affinity to living body are desirable for use.

Figure 1:
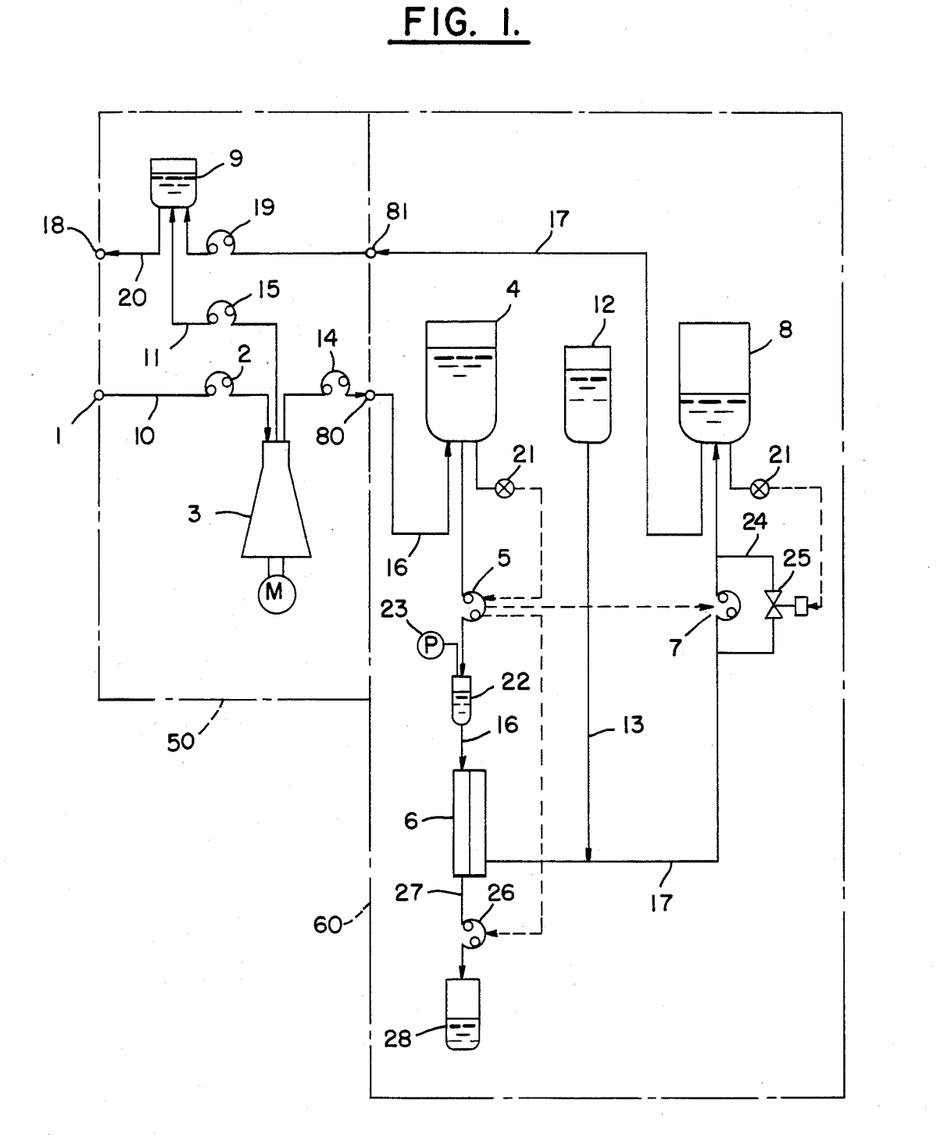
FIG. 1 is a flow-diagrammatic view of a system comprising a continuous operation type centrifugal separator and an apparatus for plasma treatment according to this invention which are connected together.

FIG. 1 is a flow-diagrammatic view of a system comprising an apparatus 60 of this invention connected to a continuous operation type centrifugal separator 50, and a description of the arrangement thereof will be made in order along the flow of blood as follows:

Blood is first fed to the bowl 3 of the centrifugal separator 50 by a pump 2 such as a roller pump, if required, through the blood inlet part 1 (that can be connected to the generally used blood letting instruments as shunt and syringe as well as blood reservoir) and the blood inlet circuit 10, and separated into a corpuscular fraction and plasma. Plasma component separated by the centrifugal separator 50 is continuously fed into the plasma treatment apparatus 60 of this invention. That is, plasma component separated by the centrifugal separator is introduced into the plasma feeding circuit 16 from the plasma inlet port 80 by the roller pump 14 incorporated in the centrifugal separator. The plasma is retained in the plasma reservoir bag 4 provided in said circuit. Means 21 for sensing the fluid level is provided within said reservoir bag 4. When plasma component is collected in quantity more than predetermined, the plasma feeding pump 5 (which can be, for example, a roller pump) controlled in association with said level sensing means operates to take out plasma fraction from the bag and delivers said fraction to the filtration membrane module 6. A drip chamber 22 having a pressure gauge 23 connected thereto is provied in the plasma feeding circuit 16 and monitors abnormal pressure caused by clogging in the filtration membrane module 6 or other troubles. When forming a system by connecting the plasma treatment apparatus 60 of this invention to the centrifugal separator, by setting a flow quantity fed by said plasma feeding pump 5 slightly larger than that fed by the roller pump 14 which discharges plasma fraction from the centrifugal separator, quick treatment of plasma fraction collecting in the plasma reservoir bag and minimization of the extracorporeal circulation quantity of blood are made possible. The plasma fraction fed to the membrane module 6 is thereby separated into high-molecular-weight substances and low-molecular-weight substances containing albumin. Purified plasma fraction constituted of low-molecular-weight substances separated by said filtration membrane module 6 is fed to the purified plasma reservoir vessel 8 provied in the purified plasma return circuit 17 by the purified plasma delivery pump 7 controlled in association with the plasma feeding pump 5. The purified plasma fraction introduced from said purified plasma reservoir vessel 8 is fed through the purified plasma outlet port 81 to a mixing device 9 by a roller pump 19 incorporated in the centrifugal separator and thereby mixed with corpuscular fraction introduced into the corpuscular fraction outlet circuit 11 by the roller pump 15 incorporated in the centrifugal separator. Purified blood as a mixture of purified plasma and corpuscular fraction is introduced from the purified blood outlet part 18 (that can be connected to the shunt, instillation set, or the like) provided in the purified blood return circuit 20. When not using the roller pump 19, the mixing device may be used as a purified plasma reservoir vessel. On the other hand, condensed plasma component containing high-molecular-weight substances separated by said filtration membrane module 6 is discharged by the condensed plasma discharge pump 26 provided in the condensed plasma discharge circuit 27 into the waste fluid vessel 28. The fluid flow quantity in the pump 26 is usually set to be equal to or under 1/5 to 1/10 of that in the plasma feeding pump 5. The aforesaid pump 26 may be controlled in association with the plasma feeding pump 5 so that a ratio between the quantity of plasma component fed into the membrane module and that of condensed plasma component delivered therefrom may always assume a predetermined value. In this case, if the fluid flow quantity in the plasma feeding pump 5 is set at 30 cc/min, the flow quantity in the plasma discharge pump is automatically adjusted to be equal to or under 1/5–1/10 of that in the former, that is, 6–3 cc/min or under. Also, said purified plasma delivery pump 7 operates to perform control in association with the plasma feeding pump 5 for setting the ratio between the plasma quantity fed to the membrane module 6 and that delivered therefrom. For example, when the flow quantity in the plasma feeding pump 5 is set at 30 cc/min, the purified plasma delivery pump is controlled to deliver the fluid in quantity of 24–30 cc/min. When the whole quantity of plasma component is filtered by the filtration membrane module, the flow quantity in said plasma feeding pump and that in the purified plasma delivery pump are set to be equal to each other. And, the condensed plasma discharge pump is stopped.

A circuit 13 for supplying a supplementary fluid such as albumin or hydroxyethyl starch (HES) from a supplementary fluid reservoir bag 12 to the purified plasma component for compensating condensed plasma component removed by said membrane module 6 may be connected to the upstream side of the purified plasma delivery pump in the purified plasma return circuit 17. In this case, by setting the flow quantity in the purified plasma delivery pump 7 so as to equalize the plasma quantity fed to the filtration membrane module 6 to the quantity of purified plasma including purified plasma fraction delivered from said module plus supplementary fluid, the supplementary fluid in the same quantity as that of the condensed plasma component discharged by the condensed plasma discharge pump 26 is poured into the purified plasma reservoir vessel 8. When providing a circuit for supplementary fluid, it is preferable to provide a by-pass circuit 24 by-passing the purified plasma delivery pump. This by-pass circuit is provided for the purpose of delivering the supplementary fluid through the by-pass to the purified plasma reservoir vessel 8 with a valve 25 opened when all pumps in the plasma treatment apparatus are stopped due to occurence of troubles such as clogging in the membrane module and resulting replacement of said module. Upon elimination of troubles, the valve 25 is closed and normal operation can be started again. Therefore, fluid transfusion into the human body can be performed without interruption even at the down-time of the apparatus, thereby ensuring a high degree of safety.

Means 21 for sensing the fluid level in the plasma reservoir bag 4 is preferably composed to be capable of constantly monitoring the fluid level because of ease in changing a level of fluid to be set. As fluid level sensing means, applicable are methods that use a pressure sensor to sense the level by pressure, methods that depend on sensing of weight, and methods that directly sense the fluid level by means of ultrasonic waves.

Figure 2:
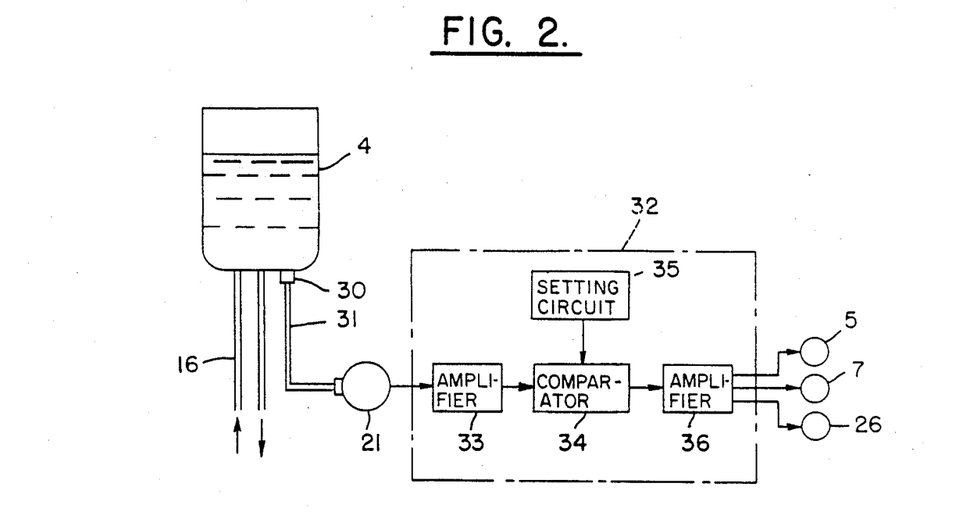
FIG. 2 is an electric circuit diagram of fluid level sensing means of plasma reservoir bag.

FIG. 2 is a representation of an example using a pressure sensor as fluid level sensing means 21, wherein a tube 31 whose inner diameter is 1 mm or less, usually 0.8 mm, is connected to the pressure sensing hole 30 provided on the lower side of the plasma reservoir bag 4 and pressure sensor 21 is fixed to the end of said tube. As a pressure sensor, a diaphragm type pressure converter is generally used. When the fluid level changes with the plasma component poured into the plasma reservoir bag, head pressure is exerted on the air contained in a thin tube and the compressed air causes displacement of the diaphragm. Minute displacement of the diaphragm is detected by a strain gauge made of metallic wire, semiconductor strain gauge, or the like whereby detected signals are transmitted to the control device 32 for controlling the operation of every pump. Signals emitted from the pressure sensor are amplified by the amplifier circuit 33 and then transmitted to the comparator circuit 34. In the comparator circuit, signals are compared with those corresponding to the fluid level set in the setting circuit 35 and transmitted to the drive circuit 36 for controlling revolutions of the pumps 5, 7, and 26. By fluid level sensing means 21, the quantity of plasma component reserved in the plasma reservoir bag 4 is sensed and, at the same time, the number of resolutions of the plasma feeding pump 5 is automatically changed under control performed in association with said sensing means, or the fluid level in the plasma reservoir bag can be controlled to be within a predetermined range by automatically turning ON—OFF the switch. For example, when the fluid level falls lower than predetermined, an adjustment may be made by retarding or once stopping the plasma feeding pump 5. Fluid level sensing means 21 may be disposed in the purified plasma reservoir vessel 8. In this case, a valve 25 provided in the circuit 24 bypassing the purified plasma delivery pump is controlled in association with fluid level sensing means. That is to say, when the fluid level in the purified plasma reservoir vessel falls lower than predetermined, the valve is opened for feeding supplementary fluid into said reservoir vessel and closed with the return of the fluid level to the initial position. Such a control effected by fluid level sensing means in association with the valve constantly keeps the quantity of purified plasma component at a predetermined level in the purified plasma reservoir vessel. Therefore, an accident such as entrance of air into the purified plasma fraction to be returned to the patient's body possibly caused by fluid shortage can completely be prevented.

As means for controlling the fluid quantity in said pumps 5, 7, and 26, those which employ a method to electrically control the number of revolutions of these pumps may be used. Further, a duplex or triplex type roller pump is also usable. In this case, an adjustment of the fluid quantity flowing in every circuit is made possible by changing the diameter of corresponding tube. As a plasma reservoir bag 4, a flexible bag having a capacity of 50 to 3,000 cc, for example, a blood bag, can be used. A flexible bag having a capacity usually ranging from 200 to 3,000 cc is used as a purified plasma reservoir bag 8, however, a vessel having a capacity of 10 to 50 cc may be used when the purified plasma fraction is returned to the patient's body by means of the purified plasma delivery pump. As a vessel as above, a drip chamber for dialysis may be used.

A mixing device is used for mixing purified plasma component with corpuscular fraction and comprises a flexible bag or drip chamber. In addition to the above-said device, a plasma warmer for warming plasma fraction cooled during extracorporeal circulation, or a prefilter for removing material substances contained in the plasma component may be provided on the upstream side of the filtration membrane module.

Figures 3, 4:
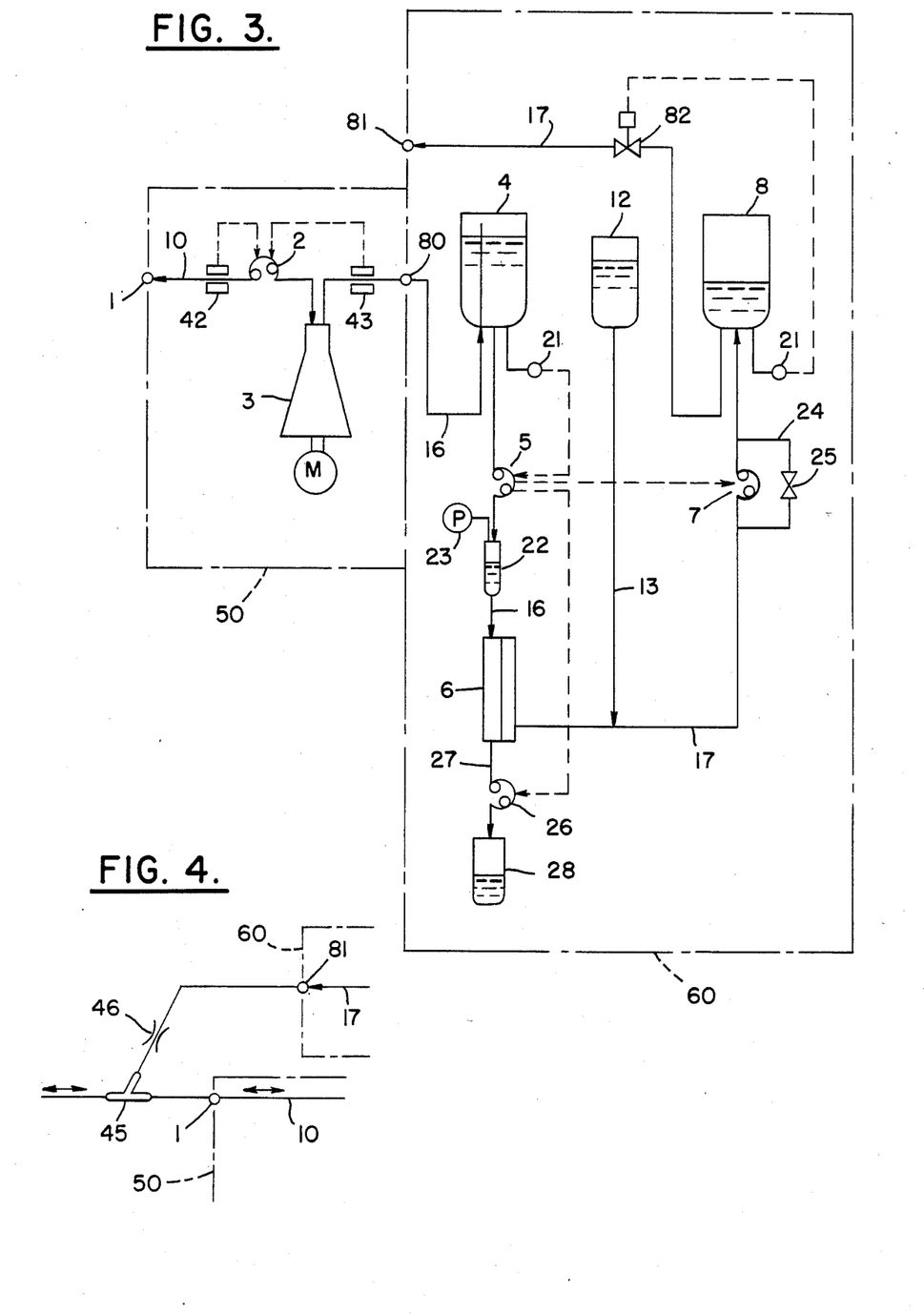
FIGS. 3 through 6 are flow-diagrammatic views of a system comprising a batch type centrifugal separator and a plasma treatment apparatus which are connected together, FIGS. 3 and 5 showing an example of an apparatus of this invention used as a part of the system depending on a two-arm method by which corpuscular fraction and purified plasma are separately returned to the human body.

FIGS. 3 through 6 are flow-diagrammatic views of a system in which a batch type centrifugal separator and a plasma treatment apparatus of this invention are combined. A different point between the batch type and the continuous operation type is such that, in the batch type one, sterilized air flows into or out from the bowl during the process of blood letting or blood returning. Namely, sterilized air filling up the centrifugal bowl 3 at the initial stage is driven out toward the plasma reservoir bag by blood introduced into the bowl at the time of blood letting but, on the contrary, at the time of blood returning, said sterilized air flowing into the bowl drives out the corpuscular fraction collected in the bowl. Accordingly, attention must be paid for preventing plasma fraction containing high-molecular-weight substances from being mixed with sterilized air flowing into the bowl during blood returning. Whereas the continuous operation type centrifugal separator depends on only a two-arm method in which different syringes are separately used for blood letting and returning, the batch type one depends on a single-arm method in which a mixture of purified plasma with corpuscular fraction is returned to the patient's body through the blood inlet port, in addition to the two-arm method using different syringes separately for blood letting and blood (or plasma) returning. FIG. 3 shows an example of a system employing the two-arm method using the plasma treatment apparatus 60 of this invention combined with the batch type centrifugal separator 50, wherein, during blood letting, blood is introduced from the blood inlet port 1 through the blood inlet circuit 10 into the bowl 3 of the centrifugal separator 50. Then, sterilized air filling the centrifugal bowl is driven out by pressurized blood fed by the pump 2, and conveyed, prior to advance of separated plasma fraction, to the plasma reservoir bag 4 through the plasma inlet port 80 and the plasma feeding circuit 16.

On the other hand, separated corpuscular fraction collects in the centrifugal bowl as it is. When the corpuscular fraction detector 43 detects that corpuscular fraction collecting in the centrifugal bowl overflows said bowl and starts flowing in the plasma feeding circuit, the apparatus is stopped for suspending blood letting and subsequent blood returning is started. At the time of blood letting, the separated plasma fraction is treated by the plasma treatment apparatus of this invention. That is, plasma fraction reserved in the plasma reservoir bag 4 is delivered to the filtration membrane module 6 in the same manner as in the case of the continuous operation type apparatus and thereby separated into high-molecular-weight substances and low-molecular-weight substances. The purified plasma fraction containing low-molecular-weight substances separated by said membrane module 6 is delivered to the purified plasma reservoir vessel 8 by the plasma fraction delivery pump 7 controlled in association with the plasma fraction delivery pump 5. Said purified plasma fraction collecting in the purified plasma reservoir vessel 8 is continuously returned to the patient's body from the purified plasma outlet port 81 provided in the purified plasma return circuit 17. In the course of blood returning, the roller pump 2 for introducing blood into the centrifugal bowl is rotated in the counter direction, when corpuscular fraction collecting in the bowl is sucked into the blood inlet circuit 10 and afterward returned to the patient's body from the blood inlet port 1 through said circuit. Such blood returning is performed by the centrifugal separator. When corpuscular fraction in the bowl is taken out, negative pressure is generated in the bowl and sterilized air filling the upper space of the plasma reservoir bag 4 is sucked into the bowl through the plasma feeding circuit 16. When corpuscular fraction is completely substituted by sterilized air sucked into the bowl and said sterilized air is further sucked into the blood inlet circuit 10 by the roller pump 2 and flows into the blood inlet circuit 10, a bubble detector 42 provided in said circuit 10 operates to stop the pump 2, thereby blood returning process also comes to an end. The above two processes as blood letting and blood returning are counted as one cycle to be repeated as many times as required. In the batch type centrifugal separator, when sterilized air in the plasma reservoir bag is sucked into the centrifugal bowl, care must be taken for preventing plasma fraction from flowing into the bowl together with sterilized air. In this invention, the plasma inlet port of the plasma reservoir bag 4 is designed so as to prevent plasma fraction from flowing into the bowl. In detail, a plasma inlet port to be connected to the plasma reservoir bag 4 is adapted to open at a position higher than that the fluid level of plasma fraction collecting in the plasma reservoir bag, that is, a position in the upper space in the bag, and a plasma outlet is adapted to open at a lower position in the bag. A plasma inlet for the plasma reservoir bag may assume a configuration extending from above and opening in the upper space in the bag or may have an independent plasma entrance passage in the bag. As a plasma reservoir bag, a blood bag sold on the market can be used after having blood inlet port thereof modified as a plasma inlet port.

In the case of a system comprising a batch type centrifugal separator and a plasma treatment apparatus of this invention which are connected together and depending on the two-arm method, it is preferable to provide a valve 82 controlled in association with fluid level sensing means 21 provided in the purified plasma reservoir vessel 8 in the purified plasma return circuit 17. On this occasion, said level sensing means is not required to operate in association with a valve 25 provided in the circuit 24 bypassing the purified plasma delivery pump 7. A cooperative operation of said level sensing means with the valve 82 enables prevention of such an accident as mixing of air with blood in the patient's body caused by fluid shortage in the purified plasma reservoir vessel.

As shown in FIG. 4, when the purified plasma outlet port 81 of the purified plasma return circuit 17 and the blood inlet port 1 of the blood inlet circuit 10 are connected to a Y-shaped connector 45 connected to the shunt or the like, a system employing the single-arm method can be obtained, whereby corpuscular fraction and purified plasma are mixed together the Y-shaped connector and returned to the patient's body. In this case, it is necessary to provide a changeover valve 46 in the circuit which connects the purified plasma outlet port 81 in the purified plasma return circuit 17 with the Y-shaped connector 45 so that purified plasma fraction is prevented from entering the centrifugal separator together with blood during blood letting. The changeover valve 46 operates in association with the corpuscular fraction detector 43 and bubble detector 42 and can automatically be controlled so as to be closed and opened at the time of blood letting and blood returning, respectively. Further, when this changeover valve 46 is controlled in association with fluid level sensing means 21 provided in the purified plasma reservoir vessel 8, an accident of entrance of air into the intra-corporeal circulation possibly caused by shortage of fluid in said reservoir vessel can be prevented.

The changeover valve 46 is preferably a pinch valve which directly clamps or opens the circuit path for preventing blood from direct contact with the passage in the valve.

Figure 5:
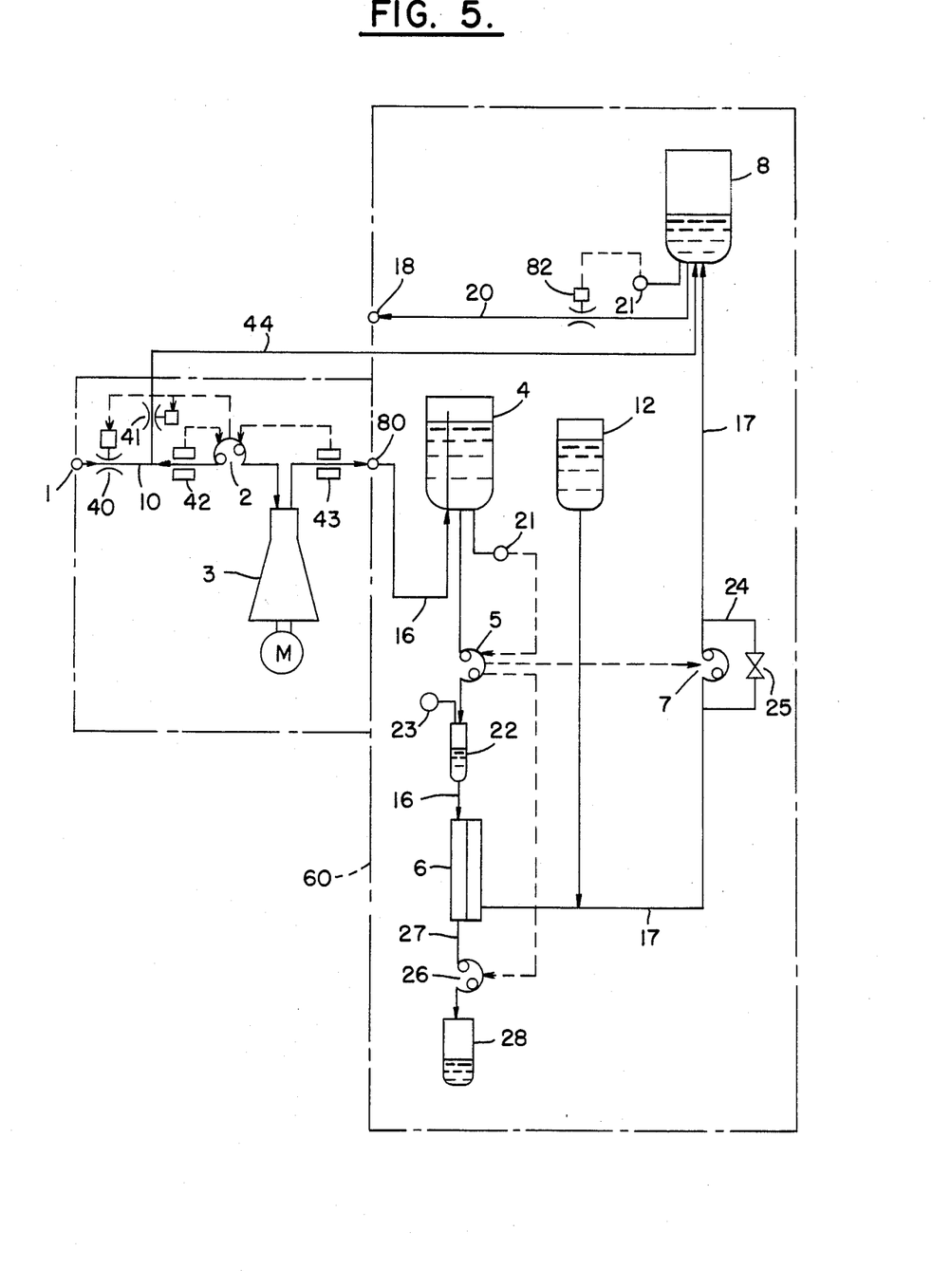

FIG. 5 is a representation of another example of the two-arm method for mixing corpuscular fraction with purified plasma component and then returning them into the patient's body, whereby the blood inlet circuit 10 is connected to the purified plasma reservoir vessel 8 by the corpuscular fraction feeding circuit 44. The corpuscular fraction feeding circuit and blood feeding circuit are adapted to be capable of being changed over properly. FIG. 5 shows that a fluid passage is so designed as to be changed over by two changeover valves 40 and 41 provided in respective circuit. Said purified plasma reservoir vessel 8 (corresponding to the blood reservoir vessel in the batch type centrifugal separator), circuits 10, 20, and 44, and changeover valves 40 and 41 belong to the centrifugal separator 50 of two-arm method type. Therefore, when the purified plasma returning circuit 17 is connected to the corpuscular fraction reservoir vessel belonging to the centrifugal separator, the corpuscular fraction reservoir vessel can be used as a purified plasma reservoir vessel. An apparatus thus arranged operates as follows:

First, a changeover valve 41 closes and the other changeover valve 40 opens for blood letting so as to introduce blood into the centrifugal separator by which blood is separated into corpuscular fraction and plasma, whereby sterilized air driven out from the bowl is reserved in the plasma reservoir bag 4 and the separated plasma component is treated by the filtration membrane module 6, thereby plasma component freed of high-molecular-weight substances being conveyed to the purified plasma reservoir vessel 8. The purified plasma fraction is continuously returned to the patient's body. When the corpuscular fraction detector 43 detects that corpuscular fraction begins to flow into the plasma feeding circuit 16, blood letting process terminates and a subsequent process to mix purified plasma with corpuscular fraction starts. In the mixing process, the changeover valve 40 closes and the other valve 41 opens, when the pump 2 rotates in the counter direction, corpuscular fraction in the centrifugal bowl is delivered to the purified plasma reservoir vessel 8 through the corpuscular fraction feeding circuit 44, and corpuscular fraction is mixed with plasma component in said reservoir vessel. When corpuscular fraction in the bowl is substituted by sterilized air and the bubble detector 42 detects that sterilized air flows out from the bowl, the mixing process terminates and blood letting process starts again.

A process of returning purified blood containing corpuscular fraction and purified plasma component in said purified plasma reservoir vessel 8 to the patient's body is conducted in parallel with blood letting as a second process at the same time. In the purified blood return circuit 20, there may be provided a changeover valve 82 to be controlled in association with fluid level sensing means 21 provided in said reservoir vessel 8 and to prevent an accident of entrance of air into the patient's body caused by fluid shortage in the purified plasma reservoir vessel.

Figure 6:
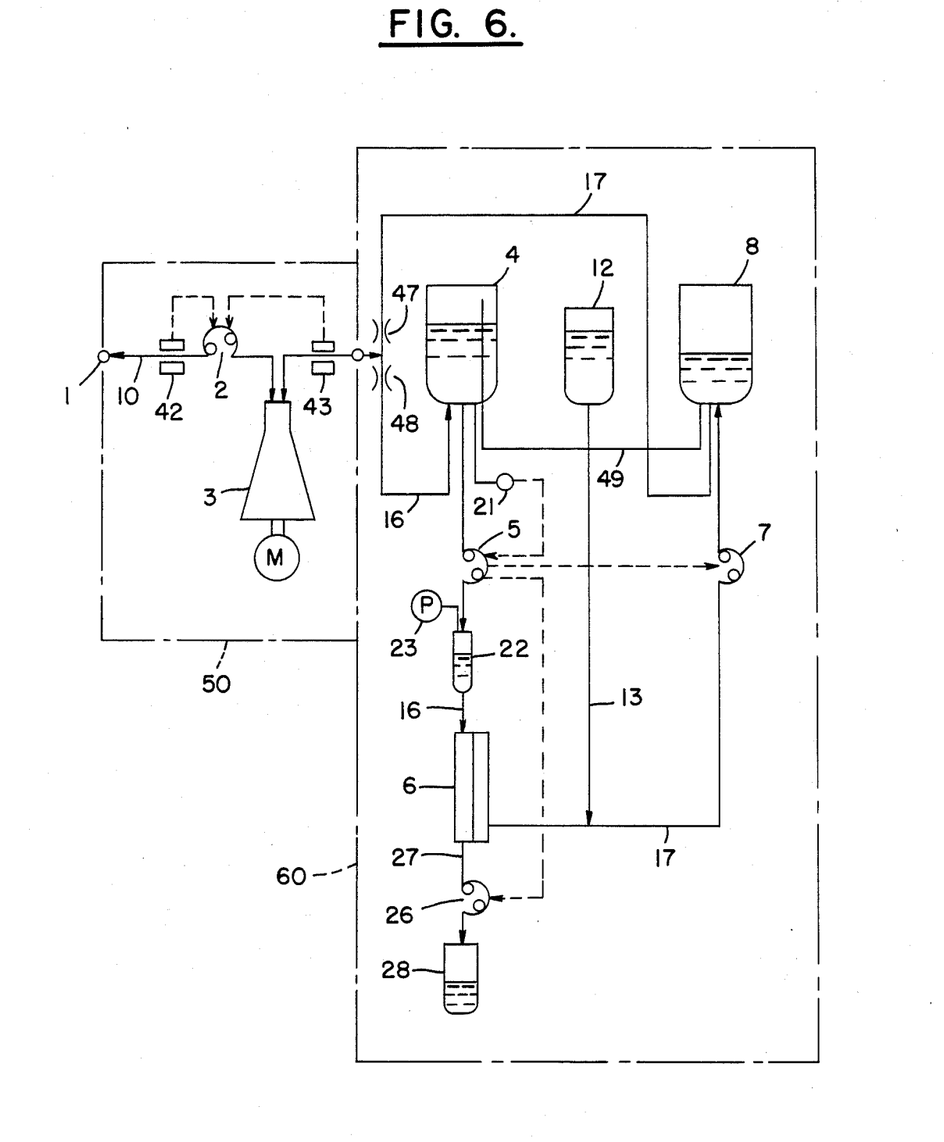

FIG. 6 is a view of an example employing the single-arm method in which a single piece of syringe is used for both blood letting and blood returning in such manner that the purified plasma return circuit 17 is connected to the plasma feeding circuit 16. These two circuits are properly changed over with each other by flow path changeover means 47,48. In the arrangement shown in FIG. 6, two changeover valves 47 and 48 provided in respective circuits operate to change over the flow paths. As flow path changeover means as above, usable are a three-way valve or two check valves as well as said two changeover valves. The apparatus shown in FIG. 6 is characterized by an arrangement that the plasma reservoir bag 4 and purified plasma reservoir vessel 8 are connected together by a communication circuit 49 for transfer of sterilized air, the apparatus operating as follows:

First, in the process of blood letting, a changeover valve 47 closes whereas the other changeover valve 48 opens and blood is introduced into the centrifugal separator 50 through the blood inlet part 1. Separated plasma fraction is collected in the plasma reservoir bag 4 through the plasma feeding circuit 16, and then purified by the filtration membrane module 6 in the same way as performed in the arrangement shown in FIG. 1. The purified plasma fraction is collected and reserved in the purified plasma reservoir vessel 8. Upon finish of blood letting, the changeover valve 48 closes whereas the other valve 47 opens and the roller pump 2 for introducing blood into the bowl rotates in the counter direction, thereby a blood returning process starts. With the revolutions of the pump 2 in the counter direction, corpuscular faction in the bowl is sucked by the roller pump 2 and returned to the patient's body through the blood inlet port 1 provided in the blood inlet circuit 10. When corpuscular fraction starts flowing out from the bowl, purified plasma fraction in the same quantity as that of the corpuscular fraction having flowed out is sucked into the bowl through the purified plasma return circuit 17 due to negative pressure generated in the bowl and, after being mixed with corpuscular fraction, returned to the patient's body. When purified plasma fraction in the purified plasma reservoir vessel 8 is entirely sucked into the bowl, sterilized air collected in the upper space in the plasma reservoir vessel 4 flows to the purified plasma reservoir vessel 8 through the communication circuit 49 and further sucked into the centrifugal bowl 3 through the purified plasma return circuit 17. Purified blood in the bowl 3 is completely substituted by sterilized air and, when said sterilized air flows from the bowl, the bubble detector 42 provided in the blood inlet circuit 10 operates, thereby the blood returning process terminates. Blood letting and blood returning processes are repeated as many times as required. In this apparatus, it is absolutely necessary to provide a communication circuit 49 for transferring sterilized air driven out into the plasma reservoir bag 4 at the time of blood letting toward the purified plasma reservoir vessel 8 so as to suck said sterilized air for complete substitution of said air with purified blood. An opening of this communication circuit connected to the plasma reservoir bag must be located in the upper space in the plasma reservoir bag 4 for preventing plasma component from being sucked into the bowl 3 together with sterilized air. Instead of said communication circuit, a suction/exhaust port to which a bacterio-repellent filter is fixed may be provided in the upper space of the purified plasma reservoir vessel 8. Fluid level sensing means is not required for the purified plasma reservoir vessel 8 in the system shown in FIG. 6. Incidentally, for simplification of the description, parts in FIGS. 3 through 6 identical to those in FIG. 1 are indicated by the same reference numerals as those in FIG. 1.

Figure 7:
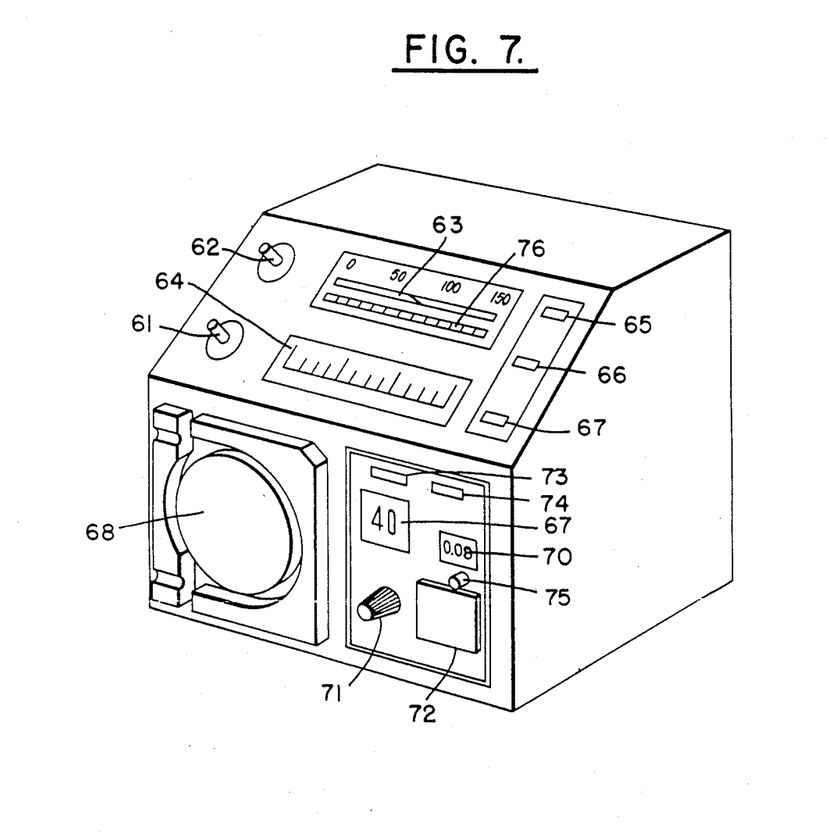

FIG. 7 is a perspective view of a monitoring unit composing a plasma treatment apparatus of this invention. The plasma feeding circuit 16 and purified plasma feeding circuit 17 are fixed to a duplex pump 68 (used in place of pumps 5 and 7) provided in the front part of the monitoring unit. A pipe 31 (shown in FIG. 2) for introducing the head pressure in the plasma reservoir bag 4 to the pressure sensor is connected to a connector 61, and another pipe for introducing the pressure in the drip chamber 22 provided in the plasma feeding circuit to the pressure gauge is connected to another connector 62. The reference numeral 63 represents a digital type level indicator for indicating the fluid level in the plasma reservoir bag 4 which indicates the head pressure in terms of bar-graph. A switch designated as 76 is intended to permit optional setting of fluid level of plasma. The numeral 64 represents a pressure gauge for indicating the pressure on the inlet side of the filtration membrane module and 71 indicates a knob for setting the flow quantity in the plasma feeding pump 5. The total quantity of plasma fraction fed to the membrane module by the abovesaid pump is indicated by the integrating indicator 70. Reference numerals 72 and 73 represent a main switch and a changeover switch respectively, which performs changeover between automatic drive to manual drive. At the time of automatic drive, a lamp 74 is lighted and the pump is rotated when the level of plasma fraction in the plasma reservoir bag exceeds a preset value. When said plasma fraction level falls below a preset value, said lamp is turned off and said pump stops rotating. The numeral 75 represents an integration resetting button. A lamp to be lighted for indicating an occurrence of abnormality is provided for said monitor. The numeral 65 designates a pressure alarm lamp to be lighted when the pressure on the inlet side of the membrane module deviates beyond the upper or lower limit set for alarming, 66 being a lamp to be lighted when the cover of the pump 68 is opened and 67 being a lamp to be lighted when the plasma quantity in the plasma reservoir bag exceeds an allowance.

Control systems of the plasma treatment apparatus of this invention are all contained in the above-said monitor unit. Therefore, the centrifugal separator and the apparatus of this invention can be controlled fully separately from each other when connected together to operate as a systematized unit.

As has been described hitherto, an apparatus according to this invention is enabled to operate as a part of a systematized unit by provision of a plasma reservoir bag 4 and purified plasma reservoir 8 bag as well as by adapting fluid level sensing means 21 in the plasma reservoir bag, a plasma feeding pump 5, and a purified plasma delivery pump 7 to be controlled in association with each other when connected to any of centrifugal separators currently used and different from each other in performance mechanism.

The use of such a system as above ensures effective and safe removal of harmful substances from blood without damage to and loss of erythrocytes and thrombocytes or loss of serum protein.

What is claimed is:

1. The method of treating plasma separated from the corpuscular fraction of blood in a continuous operation type centrifugal separator and for returning to a patient corpuscular fraction and purified plasma freed of high molecular weight substances, said method comprising the steps of:
provided a centrifugal separator;
delivering blood to said centrifugal separator;
separating the blood into a plasma fraction and a corpuscular fraction;
separating the plasma into a high molecular weight fraction and a low molecular weight fraction with a filtration membrane module;
providing a plasma feeding circuit connecting the centrifugal separator with the filtration membrane module;
disposing a plasma reservoir bag in said plasma feeding circuit between said centrifugal separator and said filtration membrane module;
continuously pumping the plasma fraction from the centrifugal separator to a plasma reservoir bag through the plasma feeding circuit at a first flow rate;
sensing the level of fluid in the plasma reservoir bag;
selectively pumping the plasma from the plasma reservoir bag at a second flow rate, higher than the first flow rate in response to the fluid level in the plasma reservoir bag being within a predetermined range;
returning the purified plasma from the filtration membrane module to the patient;
said step of returning the purified plasma, including pumping purified plasma to a purified plasma reservoir vessel;
maintaining the fluid flow rate between the plasma introduced into the filtration membrane module and the purified plasma delivered from the filtration membrane module at a predetermined, controlled value;
providing a bypass circuit around the purified plasma delivery pump;
providing a supplementary fluid reservoir supply bag to supply a supplementary fluid to the plasma return circuit at a point upstream of the purified plasma delivery pump;
discharging the high molecular weight fraction from the filtration membrane module.

2. An apparatus for treatment of plasma separated from the corpuscular fraction of blood in a batch operation type centrifugal separator and for returning the corpuscular fraction and purified plasma freed of high molecular weight substances, said apparatus comprising:
a filtration membrane module for separating the plasma into a high molecular weight fraction and a low molecular weight fraction;
a plasma feeding circuit connecting the centrifugal separator to the filtration membrane module,
a plasma reservoir bag disposed in said plasma feeding circuit and having a plasma inlet port in its upper portion, said plasma reservoir bag and said centrifugal separator being connected to form an airtight system containing sterilized air;
means for sensing the level of plasma in the plasma reservoir bag;
a plasma feeding pump disposed in said plasma feeding circuit;
means associated with said plasma feeding pump and the plasma level sensing means to fix the plasma level in the plasma reservoir bag within a predetermined range below the plasma inlet port;
a plasma return circuit connected to the filtration membrane module;
means associated with said centrifugal separator for returning the corpuscular fraction of blood with the purified plasma;
a purified plasma reservoir vessel disposed in said plasma return circuit;
a purified plasma delivery pump disposed in said plasma return circuit;
means controlling the plasma delivery pump and the plasma feeding pump to set the fluid flow ratio between plasma introduced into the filtration membrane module and purified plasma delivered from said filtration membrane module at a predetermined value;
a bypass circuit around the purified plasma delivery pump;
a supplementary fluid circuit connecting a supplementary fluid reservoir to the plasma return circuit at a point upstream of the purified plasma delivery pump;
a condensed plasma discharge circuit for discharging the high molecular weight fraction from the filtration membrane module;
a condensed plasma discharge pump disposed in said condensed plasma discharge circuit; and
means associated with the condensed plasma discharge pump to control the rate of discharge of the discharged high molecular weight fraction.

3. Apparatus according to claim 2 which additionally comprises:
means for sensing the level of fluid in the purified plasma reservoir vessel, and
a changeover valve disposed in the bypass circuit which is adapted, in association with the fluid level sensing means in the purified plasma reservoir vessel, to close when the fluid level in the purified plasma reservoir vessel falls below a predetermined value.

4. Apparatus according to claim 3 which additionally comprises:
a blood inlet circuit connected between a blood inlet and the batch type centrifugal separator;
a corpuscular fraction feeding circuit connecting the purified plasma reservoir vessel to said blood inlet circuit;
first and second changeover valves, said first changeover valve disposed in the blood inlet circuit between the blood inlet and the junction with the corpuscular fraction feeding circuit, and said second changeover valve disposed in the corpuscular fraction feeding circuit;
means for delivering the corpuscular fraction to said purified plasma reservoir;
means for opening said first changeover valve and closing said second changeover valve to deliver blood to said centrifugal separator;
means for closing said first changeover valve and opening said second changeover valve for directing the corpuscular fraction from said centrifugal separator to the means for delivering the corpuscular fraction.

5. Apparatus according to claim 2 which additionally comprises:

a blood inlet circuit connected to the batch type centrifugal separator;

a Y-shaped connector connecting the plasma return circuit to the blood inlet circuit;

means for delivering the corpuscular fraction from said centrifugal separator to said Y-shaped connection;

a changeover valve disposed in the plasma return circuit for opening and closing said plasma return circuit; and means for opening said changeover valve for plasma flow from the purified plasma reservoir to the blood inlet circuit and for feeding the corpuscular fraction to said blood inlet circuit to mix with the purified plasma.

6. An apparatus for treatment of plasma separated from the corpuscular fraction of blood in a centrifugal separator and for returning the corpuscular fraction and purified plasma freed of high molecular weight substances, said apparatus comprising:

a filtration membrane module for separating the plasma into high molecular weight substances and low molecular weight substances;

a plasma feeding circuit connecting the centrifugal separator with the filtration membrane module;

a plasma reservoir bag disposed in said plasma feeding circuit;

means for sensing the level of fluid in the plasma reservoir bag;

a plasma feeding pump disposed in said plasma feeding circuit;

means associated with said plasma feeding pump and the fluid level sensing means to fix the fluid level in the plasma reservoir bag within a predetermined range;

a plasma return circuit connected to the filtration membrane module;

a purified plasma reservoir vessel disposed in said plasma return circuit;

a purified plasma delivery pump disposed in said plasma return circuit;

means controlling the plasma delivery pump and the plasma feeding pump to set the fluid flow ratio between plasma introduced into the filtration membrane module and purified plasma delivered from said filtration membrane module at a predetermined value;

an airtight communication circuit between the purified plasma reservoir vessel and the plasma reservoir bag, said airtight communication circuit containing sterilized air and having a port in the plasma reservoir bag at a level above the level of fluid in said bag;

first and second changeover valves, the first changeover valve disposed in the plasma feeding circuit between said centrifugal separator and said plasma reservoir bag;

the second changeover valve disposed in the plasma return circuit between said purified plasma reservoir vessel and the centrifugal separator;

means for alternatively opening said first changeover valve and closing said second changeover valve to deliver the plasma fraction from said centrifugal separator to said plasma reservoir bag and for opening said second changeover valve and closing said first changeover valve for returning the purified plasma from said purified plasma reservoir vessel to said centrifugal separator;

a condensed plasma discharge circuit for discharging the high molecular weight substances from the filtration membrane module;

a condensed plasma discharge pump disposed in said condensed plasma discharge circuit; and means associated with the plasma discharge pump to control the rate of discharge of the discharged high molecular weight substances.

* * * * *